United States Patent [19]

Orzalesi

[11] 4,423,053
[45] Dec. 27, 1983

[54] DERIVATIVES OF 2-AMINO-5-(O-SULPHAMIDOPHENYL)-1,3,4-THIADIAZOL AS ANTIVIRAL AGENTS AND A PROCESS FOR THE PREPARATION THEREOF

[75] Inventor: Giovanni Orzalesi, Florence, Italy

[73] Assignee: Societa Italo-Britannica L. Manetti-H. Roberts & Co., Florence, Italy

[21] Appl. No.: 358,561

[22] Filed: Mar. 16, 1982

[30] Foreign Application Priority Data

Mar. 18, 1981 [IT] Italy .............................. 48047 A/81

[51] Int. Cl.³ .................. A61K 31/41; C07D 285/12
[52] U.S. Cl. ..................................... 424/269; 548/138
[58] Field of Search ....................... 548/138; 424/269

[56] References Cited

U.S. PATENT DOCUMENTS 4,265,898  5/1981  Horstmann et al. ................ 548/138

FOREIGN PATENT DOCUMENTS 615421  2/1961  Canada .............................. 548/138

Primary Examiner—Mary C. Lee
Attorney, Agent, or Firm—Ladas & Parry

[57] ABSTRACT

Compounds which are derivatives of 2-amino-5-(o-sulphamidophenyl)-1,3,4-thiadiazol of formula

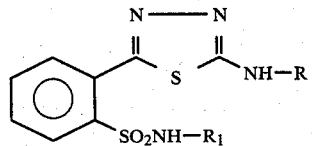

wherein R is a hydrogen atom or a —CH$_3$, —C$_2$H$_5$, iso—C$_3$H$_7$, n—C$_4$H$_9$ or —CH$_2$—CH=CH$_2$ group and R$_1$ is a hydrogen atom or a —CH$_3$ or —C$_2$H$_5$ group, are active agents against virus infections in higher animal organisms.

11 Claims, No Drawings

DERIVATIVES OF 2-AMINO-5-(O-SULPHAMIDOPHENYL)-1,3,4-THIADIAZOL AS ANTIVIRAL AGENTS AND A PROCESS FOR THE PREPARATION THEREOF

The present invention refers to organic compounds showing a pharmaceutical activity, which are capable of counteracting in a specific and selective way the virus infections in cells of higher animal organisms, such as warm blood vertebrates, including man. The invention moreover relates to a process for obtaining said new compounds by synthesis.

This invention relates also to the pharmaceutical application of said compounds as active agents for the treatment of said virus infections, as well as their use in pharmaceutical compositions.

The chemical compounds of the present invention are derivatives of a 5-substituted 2-amino-1,3,4-thiadiazol radical.

An object of the present invention is therefore antiviral active agents consisting of the new compounds of the general formula

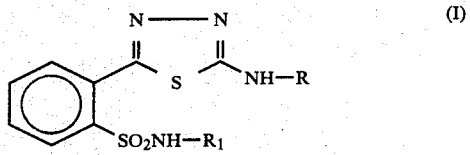

wherein R and $R_1$ represent a hydrogen atom or the following organic groups.

| R | $R_1$ |
|---|---|
| (a) —$CH_3$ | (a) —$CH_3$ |
| (b) —$C_2H_5$ | (b) —$CH_2H_5$ |
| (c) -iso-$C_3H_7$ | |
| (d) -n-$C_4H_9$ | |
| (e) —$CH_2$—CH=$CH_2$ | |

In the above compounds a tautomeric resonance can exist between the nitrogen atom of the —NH—R group and the adjacent one, in the 3 position of thiadiazol radical, with a shifting of the hydrogen atom and of the double link.

PREPARATION

The products according to the present invention are all obtained starting from the well known o-sulphobenzoimide (compound III), with a desired substituent in $R_1$, which is reacted with phosphor pentasulphide in the presence of pyridine or a different unsaturated organic base of the same type.

The thioderivative obtained (compound II) is reacted with a suitable thiosemicarbazide, in turn having the desired substituent in R, said successive reaction being made to take place in the presence of n-butanol or a different organic polar solvent of a similar type, so that the compound I is obtained.

A further object of the invention is the above illustrated process of preparation, which is chemically defined by way of the following reactions

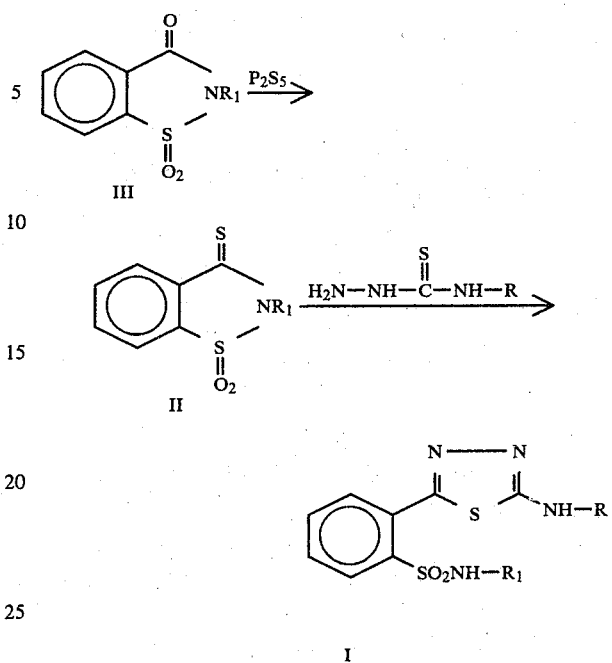

For a purely exemplificative and not limitative purpose in the following some examples of preparation of the compounds according to the invention are illustrated.

EXAMPLE 1

Preparation of compound II ($R_1$=H)

0.01 moles of o-sulphobenzoimide (pure saccharin) are dissolved in 30 ml of anhydrous pyridine and the solution is reacted with 0.012 moles of $P_2S_5$, the reaction mixture being refluxed for 3 hours. The solvent is distilled off and the dry residue is then extracted with chloroform. The chloroform extracts are collected and dried on $MgSO_4$, then the chloroform is distilled off and again a dry residue is obtained. This is crystallized from ethanol, giving compound II in the form of its pyridine salt:

Melting point: 144° C. at the Kofler bench.

Analysis %: Found: C,51.91; H,3.76; N,9.94. Calculated: C,51.79; H,3.59; N,10.07.

EXAMPLE 2

Preparation of compound II ($R_1$=—$CH_3$)

0.01 moles of N-methyl-saccharin are dissolved in 3 ml of anhydrous pyridine and the solution is reacted with 0.012 moles of $P_2S_5$, the reaction mixture being refluxed for 3 hours. The solvent is distilled off and the dry residue is extracted by chloroform. The chloroform extracts are collected and dried on $MgSO_4$ then the chloroform is distilled off, giving a dry residue again.

This is crystallized from ethanol:

Melting point: 182° C. at the Kofler bench.

Analysis %: Found: C,44.98; H,3.01; N,6.67. Calculated: C,45.07; H,3.28; N,6.57.

EXAMPLE 3

Preparation of compound I (R=$R_1$=H)

0.0035 moles of compound II, previously obtained as pyridine salt, are dissolved in 50 ml of n-butanol and the solution is reacted with 0.0076 moles of thiosemicarbazide, the reaction mixture being refluxed for 3 hours substituents R and/or $R_1$ obtained by resorting to the corresponding N-alkylthiosemicarbazide.

| Compound (short denomination) | | (structure with $SO_2NH-R_1$ and $NH-R$) | Melting point |
|---|---|---|---|
| G-413 | | R = H | 228° C. |
| G-444 | | R = —CH₃ | 187° C. |
| G-480 | | R = —C₂H₅ | 262° C. |
| G-512 | $R_1$ = H | R = -iso-C₃H₇ | 251° C. |
| G-513 | | R = -n-C₄H₉ | 226° C. |
| G-445 | | R = —CH₂—CH=CH₂ | 179° C. |
| G-502 | | R = H | 194° C. |
| G-514 | | R = —CH₃ | 153° C. |
| G-515 | | R = —C₂H₅ | 210° C. |
| G-516 | $R_1$ = —CH₃ | R = -iso-C₃H₇ | 206° C. |
| G-517 | | R = -n-C₄H₉ | 180° C. |
| G-518 | | R = —CH₂—CH=CH₂ | 143° C. |
| G-519 | | R = H | 160° C. |
| G-520 | | R = —CH₃ | 175° C. |
| G-521 | | R = —C₂H₅ | 193° C. |
| G-522 | $R_1$ = —C₂H₅ | R = -iso-C₃H₇ | 189° C. |
| G-523 | | R = -n-C₄H₉ | 174° C. |
| G-524 | | R = —CH₂—CH=CH₂ | 137° C. | under nitrogen stream and stirring. The solvent is distilled off and the residue is take by distilled water. It is filtered and crystallized from ethanol:

Melting point: 228° C. at the Kofler bench.

Analysis %: Found: C,37.62; H,3.21; N,21.74. Calculated: C,37.50; H,3.12; N,21.87.

EXAMPLE 4

Preparation of compound I (R=—CH₃;R₁=H)

0.0035 moles of compound II, previously obtained as pyridine salt, are dissolved in 50 ml of n-butanol and the solution is reacted with 0.0076 moles of N-methylthiosemicarbazide, the reaction mixture being refluxed for 3 hours under nitrogen stream and stirring. The solvent is distilled off and the residue is taken by distilled water. It is filtered and crystallized from ethanol:

Melting point: 187° C. at the Kofler bench.

Analysis %: Found: C,39.86; H,3.59; N, 20.90. Calculated: C,40.00; H,3.73; N,20.73.

EXAMPLE 5

Preparation of compound I (R=H; R₁=—CH₃)

0.035 moles of compound II (R₁=—CH₃) are dissolved in 50 ml of n-butanol and the solution is reacted with 0.076 moles of thiosemicarbazide, the reaction mixture being refluxed for 3 hours under nitrogen stream and stirring. The solvent is distilled off and the residue is taken by distilled water. It is filtered and crystallized from ethanol:

Melting point 194° C. at the Kofler bench.

Analysis %: Found: C,40.09; H,3.81; N,20.66. Calculated: C,40.00; H,3.73; N,20.73.

EXAMPLE 6

Following the same procedures as described in the preceding examples, the remaining new compounds of the present invention are prepared by substituting thiosemicarbazide and N-methylthiosemicarbazide in the various reactions by the homologue reactant which corresponds to the desired product.

In the following table the melting points at the Kofler bench are referred to for the compounds I having as In all cases the compounds so obtained have shown at the elemental centesimal analysis results which correspond to the theoretical values and their IR spectrums confirm the respective structure.

PHARMACOLOGICAL ANTIVIRAL ACTIVITY

The compounds of the present invention are useful and effective antiviral agents in warm blood vertebrates and in man.

Tests of antiviral activity have been brought out by using different active compounds of the invention, on different virus strains.

In the following, tests are described wherein compound G-413 (R=R₁=H) was used.

It was previously ascertained that the compound of the invention was absolutely non toxic to the cells used in the tests, every other condition being the same.

The tests were carried out inoculating virus of various kinds on living cells from different sources, forming the respective culture in tissue culture flasks, according to the method well known to those skilled in the art.

The virus forms a plurality growing seats on the bottom of the tissue culture flasks, depending on the virus concentration and the test conditions, said seats being easily identifiable with the naked eye. In such a way it is possible to establish the controls. At the same time in the tissue culture flasks wherein the compound of the invention had been introduced, at various concentrations, an inhibition is observed, as shown by a number of growing seats lower than that of the controls. Said inhibition was calculated in percent as referred in the following tables.

TESTS OF ANTIVIRAL ACTIVITY "IN VITRO"

Tests have been effected by using virus Herpes simplex, type 2 (HSV2), and virus Coxackie B, type 4 (COXB4).

The results are referred to in the following tables A and B.

TABLE A

Activity "in vitro" of G-413 in different doses on Herpes simplex virus type 2.

| | | |
|---|---|---|
| HSV2 $10^{-3}$ | 10,5 PFU/ml | |
| HSV2 $10^{-3}$ + 40,0 µg G-413 | 5,0 PFU/ml 52,4% | inhibition |
| HSV2 $10^{-3}$ + 30,0 µg G-413 | 5,0 PFU/ml 52,4% | " |
| HSV2 $10^{-3}$ + 20,0 µg G-413 | 3,0 PFU/ml 71,5% | " |
| HSV2 $10^{-3}$ + 10,0 µg G-413 | 2,0 PFU/ml 81,0% | " |
| HSV2 $10^{-3}$ + 5,0 µg G-413 | 3,5 PFU/ml 66,7% | " |
| HSV2 $10^{-3}$ + 2,5 µg G-413 | 3,5 PFU/ml 66,7% | " |

TABLE B

Activity of G-413 in different doses on Coxackie B, type 4.

| | | |
|---|---|---|
| COXB4 $10^{-6}$ | 33,0 PFU/ml | |
| COXB4 $10^{-6}$ + 20,0 µg G-413 | 6,5 PFU/ml 80,4% | inhibition |
| COXB4 $10^{-6}$ + 10,0 µg G-413 | 6,5 PFU/ml 81,9% | " |
| COXB4 $10^{-6}$ + 5,0 µg G-413 | 3,0 PFU/ml 89,9% | " |
| COXB4 $10^{-6}$ + 2,5 µg G-413 | 23,5 PFU/ml 28,8% | " |

All controls in the three tests turned out to be optimum to the standard requirements.

From tables A and B a very high percent inhibition is noted at a dose of 10 µg G-413 for HSV2 and 5 µg G-413 for COXB4.

In order to ascertain the activity of compound G-413 "in vitro" at a dose of 10 µg on Herpes simplex virus type 2 for different times of administration, a test was effected introducing the compound into the cells after the virus infection.

The results are referred in the following table C.

TABLE C

| | | | |
|---|---|---|---|
| HSV2 $10^{-2}$ | | 20,0 PFU/ml | |
| HSV2 $10^{-2}$ + 10 µg | G 413 | 7,5 PFU/ml 62,5% | inhibition |
| HSV2 $10^{-2}$ 1 h later + 10 µg | G 413 | 11,0 PFU/ml 45,0% | " |
| HSV2 $10^{-2}$ 2 h later + 10 µg | G-413 | 8,0 PFU/ml 60,0% | " |
| HSV2 $10^{-2}$ 4 h later + 10 µg | G-413 | 4,5 PFU/ml 77,0% | " |
| HSV2 $10^{-2}$ 8 h later + 10 µg | G-413 | 3,0 PFU/ml 85,0% | " |
| HSV2 $10^{-2}$ 20 h later + 10 µg | G-413 | 11,5 PFU/ml 42,5% | " |

It is appreciated that a maximum inhibition is obtained by an administration effected about 8 hours after the introduction of the virus infection.

TEST OF INHIBITION OF THE VIRION PRODUCTION

The activity of the compound G-413 was assessed by the test of inhibition of virion production.

A sample containing $10^6$ cells at 20° C. for 1 hour was infected by a plurality of infection corresponding to 10 infectant units per cell. The infected sample was washed 3 times in HBSS and incubated at 37° C. The active compound was added at the O.P.I. time; after 24 hours the whole culture was freezed and defreezed from $-70°$ to $+20°$ C. for 3 times and the cell residues were removed by centrifugation at 3000 r.p.m. for 3 minutes. The virion infectant units were determined by the method of titration in plates according to Dulbecco.

The test was effected with various types of virus, on HEp-2 cells.

The results are referred in the following tables.

TABLE D

Virion production of Polio 1 in the presence of G-413 (G-413 20 µg per "Falcon").

| | | |
|---|---|---|
| Polio 1 $10^{-6}$ | 355 PFU | |
| Polio 1 $10^{-7}$ | 267 PFU | |
| Polio 1 $10^{-8}$ | 169 PFU | |
| Polio 1 G-413 $10^{-6}$ | 29 PFU 91,9% | inhibition |
| Polio 1 G-413 $10^{-7}$ | 5 PFU 98,2% | " |
| Polio 1 G-413 $10^{-8}$ | 4 PFU 97,7% | " |

TABLE E

Virion production of ECHO 2 in the presence of G-413.

| | |
|---|---|
| ECHO 2 $10^{-6}$ | 23 PFU |
| ECHO 2 $10^{-7}$ | 20 PFU |
| ECHO 2 $10^{-8}$ | 11 PFU |
| ECHO 2 G-413 | $10^{-6}$; $10^{-7}$; $10^{-8}$ PFU 100% inhibition |

TABLE F

Virion production of Coxsackie B4 in the presence of G-413.

| | | |
|---|---|---|
| COX B4 $10^{-4}$ | 50 PFU | |
| COX B4 $10^{-5}$ | 43 PFU | |
| COX B4 $10^{-6}$ | 40 PFU | |
| COX B4 G-413 $10^{-4}$ | 14 PFU 72,0% | inhibition |
| COX B4 G-413 $10^{-5}$ | 7 PFU 83,7% | " |
| COX B4 G-413 $10^{-6}$ | 6 PFU 85,0% | " |

TABLE G

Virion production of HSV2 in the presence of G-413.

| | | |
|---|---|---|
| HSV2 $10^{-1}$ | 31 PFU | |
| HSV2 $10^{-2}$ | 20 PFU | |
| HSV2 $10^{-3}$ | 8 PFU | |
| HSV2 G-413 $10^{-1}$ | 8 PFU 75,2% | inhibition |
| HSV2 G-413 $10^{-2}$ | 5 PFU 75,0% | " |
| HSV2 G-413 $10^{-3}$ | 3 PFU 62,5% | " |

TABLE H

Virion production of Adeno 17 in the presence of G-413.

| | | |
|---|---|---|
| Adeno 17 $10^{-4}$ | 100 PFU | |
| Adeno 17 $10^{-5}$ | 83 PFU | |
| Adeno 17 $10^{-6}$ | 60 PFU | |
| Adeno 17 G-413 $10^{-4}$ | 35 PFU 65,0% | inhibition |
| Adeno 17 G-413 $10^{-5}$ | 27 PFU 67,5% | " |
| Adeno 17 G-413 $10^{-6}$ | 22 PFU 63,4% | " |

TESTS FOR THE ACTIVITY OF COMPOUND G-413 ON KIDNEY PRIMARY CELLS OF RABBIT WITH RESPECT TO HSV2

Such a cell system was selected for effecting the tests, in order to differentiate the activity of a concentration of compound G-413 in the presence of different cell systems. The same procedure was followed as described in the test of inhibition of the virion production above illustrated.

The results are referred in the following table I.

TABLE I

| | | |
|---|---|---|
| HSV2 $10^{-1}$ | 21 PFU | |
| HSV2 $10^{-2}$ | 9 PFU | |
| HSV2 $10^{-3}$ | 4 PFU | |
| HSV2 + 10 µg G-413 $10^{-1}$ | 13 PFU 38,1% | inhibition |
| HSV2 + 10 µg G-413 $10^{-2}$ | 7 PFU 23,0% | " |
| HSV2 + 10 µg G-413 $10^{-3}$ | 2 PFU 50,0% | " |
| HSV2 + 50 µg G-413 $10^{-1}$ | 6 PFU 71,5% | " |
| HSV2 + 50 µg G-413 $10^{-2}$ | 3 PFU 77,0% | " |
| HSV2 + 50 µg G-413 $10^{-3}$ | 1 PFU 75,0% | " |

The same test was carried out on kidney secondary cells of rabbit YRK, and the results are referred in the following table J.

TABLE J

| | | | |
|---|---|---|---|
| HSV2 $10^{-2}$ | | 10 PFU | |
| HSV2 $10^{-2}$ + 5 μg G-413 | | 9 PFU 10% | inhibition |
| HSV2 $10^{-2}$ + 10 μg G-413 | | 7 PFU 30% | " |
| HSV2 $10^{-2}$ + 25 μg G-413 | | 6 PFU 40% | " |
| HSV2 $10^{-2}$ + 50 μg G-413 | | 3 PFU 70% | " |
| HSV2 $10^{-2}$ + 100 μg G-413 | | 3 PFU 70% | " |

The following are tests of antiviral activity of compounds according to the invention of formula I, wherein the substituent R is a methyl radical (compound G-444) or an allyl radical (compound G-445), respectively.

The test of Polio 1 virion production on HEp-2 in the presence of G-444 and G-445 according to the method previously described in the test of virion production, has shown the results referred in the following table K.

TABLE K

| | | |
|---|---|---|
| Polio 1 $10^{-6}$ | 321 PFU | |
| Polio 1 $10^{-7}$ | 253 PFU | |
| Polio 1 $10^{-8}$ | 113 PFU | |
| Polio 1 $10^{-6}$ + G-444 | 113 PFU 64,8% | inhibition |
| Polio 1 $10^{-7}$ + G-444 | 87 PFU 65,7% | " |
| Polio 1 $10^{-8}$ + G-444 | 83 PFU 26,6% | " |
| Polio 1 $10^{-6}$ + G-445 | 85 PFU 73,6% | " |
| Polio 1 $10^{-7}$ + G-445 | 68 PFU 73,2% | " |
| Polio 1 $10^{-8}$ + G-445 | 63 PFU 44,3% | " |

TESTS OF ANTIVIRAL ACTIVITY "IN VIVO"

The activity "in vivo" of the compounds of the invention was assessed for HSV2 grafted on a rabbit cornea and by observation the development the corneal lesions.

The compounds under test were applied twice a day and after 8 days a final examination was made. Said examination showed that in the left eye (treated) a complete remission of the alteration was observed, while in the right eye (not treated) the initial dendritic formations developped to an ulceration with overlaid leucomas. At this stage the animals were sacrificed and the eyeballs were extracted. The eyeballs were homogenized and centrifugated. The viral titer was then determined on the supernatant liquid.

The results can be summarized as follows:
Control eye: titer HSV-2 = $4 \times 10^6$ PFU/ml
Treated eye: titer HSV-2 = $1 \times 10^1$ PFU/ml The results show that the treatment with the ophthalmic cream, in addition to causing an interruption of the development of the keralytic process (assessed by previous coloration with fluorescin), effects also an inhibition, in vivo, of the virus reproduction, as assessed by the fact that in the treated eye the viral titer is lower than $1 \times 10^1$ PFU ml.

CLINICAL TESTS OF ANTIVIRAL ACTIVITY

Preliminary clinical tests were effected with the compounds of the invention for topic and systematic (oral) use on voluntary patients affected by:
herpes zooster (topic and systematic use);
viral hepatitis of type B (systematic use);
oncology (patients having prevalently a metastasized lung CA and a mammary CA),
at a dosage of 5 to 3000 mg/die per os and 5 to 3000 mg/die for topic use. A therapeutical activity in comparison with non treated subjects, was assessed by clinical and body fluid examinations. In fact, for the type B hepatitis, the treatment with the usual medicines was reduced by about 10 days and at the same time the standards of SGPT and SGOT, γ-globulines, alkaline pHA, bilirubinaemia and VES turned to normal values.

With respect to herpes zooster, the vesiculas and the painful symptoms disappear in a very few days in comparison to patients treated with the usual medicines, which, for obtaining the same disappearance of the painful and cutaneous symptomathology, usually require about 20 days.

The examination of the body fluids does not show anything of interest, since the starting values fell into normality; there is only to point out a non-significant increase of the γ-globulines.

In the oncological field, the patients treated with the pharmaceutical agent of the invention, at the highest dosage, show a higher resistance to overlaid bacterial infections, hence a better clinical course confirmed by a γ-globuline increase of T-lymphocytes and β-lymphocytes, which suggests also an immunity stimulating activity of the compounds of the invention.

ACUTE TOXICITY TESTS

The acute toxicity has been tested on male and female mice of Swiss strain, having an average weight of 20±2 g, on male and female rats of Wistar strain, having an average weight of 150±10 g, and on male and female Beagle dogs.

The compounds of the invention under test were administered orally to lots of 10 animals, in the form of 0.8% suspension in Tween 80.

The animals were kept under observation for 7 days and the determination of $DL_{50}$ was effected by a graphic method: the toxicity values were higher than 1500 mg/kg in mice and higher than 3000 mg/kg in rats and dogs.

An inspective examination of the animals and an anatomical-pathological observation of dead animals shows the following facts:
the toxic symptomathology was prevalently of the excitatory type;
no noticeable alterations were noted of the digestive apparatus in the animals which died in the first 24 hours;
differences of response depending on the sex were of low importance.

SUBACUTE TOXICITY TESTS

Tests of subacute toxicity effected with some of the compounds on rat and on dog for 90 days, through two routes of administration, at three dosage levels (from 50 to 800 mg/kg/die) have further shown a low toxicity of the same compounds after a repeated treatment.

The results referred to above, in combination with the absence of toxicity of the compounds according to the invention with respect to living cells, make said compounds useful for the treatment of viral infections of different origin.

To this end the compounds according to the invention can be used as active agents in pharmaceutical compositions, wherein they are contained, together with pharmaceutically acceptable excipients.

Said compositions can be in the form of dosage units containing 5 to 500 mg of the active compound, to be administered at a rate of 5–3000 mg/die of active agent.

The composition can be administered orally in a dose containing 5 to 500 mg of active agent, at a rate of 25–3000 mg/die.

The composition can be administered parenterally in a dose containing 5 to 50 mg of active agent, at a rate of 5–200 mg/die.

The pharmaceutical compositions can be prepared in the form of tablets, coated tablets, emulsions, powders, capsules, syrups, ointments, injection solutions or suppositories for oral, parenteral, rectal or topical administration.

I claim:

1. A compound of the formula

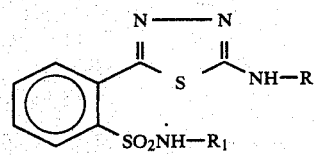

wherein R is a hydrogen atom, or a methyl, ethyl, isopropyl, n-butyl or allyl group and wherein $R_1$ is a hydrogen atom, or a methyl or ethyl group.

2. A method of preparing a compound of formula

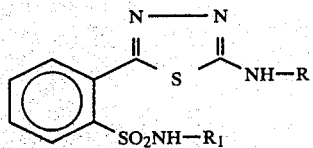

wherein R is a hydrogen atom, a methyl, ethyl, isopropyl, n-butyl, or allyl group and wherein $R_1$ is a hydrogen atom, or a methyl or ethyl group, which comprises:

(a) reacting a compound of formula

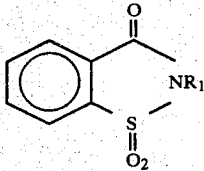

wherein $R_1$ has the above specified meaning, with phosphorus pentasulphide in the presence of pyridine at a temperature sufficient to form a salt of pyridine or said analogous base of a compound of formula

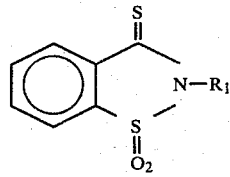

(b) reacting said salt with a substituted thio-semicarbazide of formula

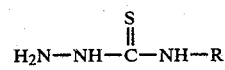

wherein R has the above specified meaning, in the presence of butanol or an analogous organic polar solvent at a temperature sufficient to form the corresponding compound of formula (I); and (c) recovering said compound from the mixture.

3. A pharmaceutical composition for the therapeutical treatment of virus infections in warm blood vertebrates, characterized in that it comprises as an active ingredient a therapeutically effective amount of a compound of formula I as defined in claim 1, in association with a pharmaceutical carrier or excipient.

4. A composition as claimed in claim 3 in the form of tablets, coated tablets, emulsions, powders, capsules, syrups, ointments, injection solutions or suppositories.

5. A composition as claimed in claim 3 in the form of dosage units wherein each dosage unit contains from 5 to 500 mg of the active ingredient.

6. A composition as claimed in claim 3 in the form of dosage units for parenteral administration, wherein each dosage unit contains from 5 to 50 mg of the active ingredient.

7. A composition as claimed in claim 3 which is adapted for topical administration.

8. A method of treating virus infections in warm blood vertebrates which comprises the administration of a therapeutically effective amount of a composition as claimed in claim 1.

9. A method of treatment as claimed in claim 8, wherein the infecting virus is Herpes simplex type 2 (HSV2), Coxackie B type 4 (COXB4), Polio 1, ECHO 2 or Adeno 17.

10. A method as claimed in claim 8, wherein the infection is Herpes Zooster or type B Viral Hepatitis.

11. A method as claimed in claim 8, wherein said amount is 5 to 3000 mg/day.

* * * * *